(12) United States Patent
Martinez et al.

(10) Patent No.: US 6,711,957 B2
(45) Date of Patent: Mar. 30, 2004

(54) SYSTEMS & METHODS FOR AUTOMATING ASPHALT MIX DESIGN

(75) Inventors: David Frederick Martinez, Cypress, TX (US); Elias George Eldahdah, Houston, TX (US)

(73) Assignee: Atser, Inc., Houston, TX (US)

( * ) Notice: Subject to any disclaimer, the term of this patent is extended or adjusted under 35 U.S.C. 154(b) by 0 days.

(21) Appl. No.: 10/155,484

(22) Filed: May 24, 2002

(65) Prior Publication Data

US 2003/0217604 A1 Nov. 27, 2003

(51) Int. Cl.[7] .................................................. G01N 3/08
(52) U.S. Cl. ........................................................ 73/824
(58) Field of Search ........................ 73/815, 813, 824, 73/841, 818, 795, 843; 250/358.1; 700/97

(56) References Cited

U.S. PATENT DOCUMENTS

| | | | | |
|---|---|---|---|---|
| 5,456,118 A | * | 10/1995 | Hines et al. | ................... 73/818 |
| 5,606,133 A | * | 2/1997 | Hines et al. | ................... 73/824 |
| 5,943,234 A | * | 8/1999 | Martinez et al. | ........ 364/468.03 |
| 6,492,641 B1 | * | 12/2002 | Dep et al. | ................ 250/358.1 |

* cited by examiner

*Primary Examiner*—Edward Lefkowitz
*Assistant Examiner*—Octavia Davis
(74) *Attorney, Agent, or Firm*—Tran & Associates

(57) ABSTRACT

Systems and methods are disclosed for automating asphalt mix design by estimating volumetric properties for one or more mix designs; running one or more tests on the mix design using a gyratory compactor; digitally collecting data for each gyration from the gyratory compactor; and selecting an optimum mix based on the gyration data.

20 Claims, 3 Drawing Sheets

SYSTEMS & METHODS FOR AUTOMATING ASPHALT MIX DESIGN

BACKGROUND

The invention relates to Superpave Asphalt Mix design.

The design of asphalt paving mixes mainly involves selecting and proportioning materials to obtain the desired properties in the finished construction. The overall objective for the design of asphalt paving mixes is to determine an economical blend of binder and gradation of aggregates, within the limits of the project specifications, and an asphalt paving mixture that yields a mix having: sufficient asphalt to ensure a durable pavement; sufficient mix stability to satisfy the demands of traffic without distortion or displacement; sufficient voids in the total compacted mix to allow for a slight amount of additional compaction under traffic loading without flushing, bleeding, and loss of stability, yet low enough to minimize the intrusion of harmful air and moisture; and sufficient workability to permit efficient placement of the mix without segregation.

From October 1987 through March 1993, a DOT program known as Strategic Highway Research Program (SHRP) conducted research effort to develop new ways to specify, test, and design asphalt materials. The final product of the SHRP asphalt research program is a system referred to as Superpave, which stands for Superior Performing Asphalt Pavements. It represents an improved system for specifying the components of asphalt concrete, asphalt mixture design and analysis, and asphalt pavement performance prediction.

Superpave mix design is a structured approach consisting of the following four steps:

selection of materials, selection of design aggregate structure, selection of design asphalt binder content, and evaluation of moisture susceptibility.

The selection of materials is accomplished by first selecting a Performance Grade asphalt binder for the project climate and traffic conditions. Superpave binders are designated with a high and low temperature grade, such as PG 64-22. For this binder, "64" is the high temperature grade and is the 7-day maximum design pavement temperature in degrees centigrade for the project. The low temperature grade, "−22," is the minimum pavement design temperature in degrees centigrade. Both high and low temperature grades are established in 6-degree increments. Thus, the binder grade is an indication of the project-specific temperature extremes for which the asphalt mixture is being designed.

In addition to climate, traffic speed and traffic level may also influence Superpave binder selection. A project with slow moving or stationary traffic would require a binder with one or two higher temperature grades than would otherwise be selected on the basis of climate alone. Projects with very high traffic levels in excess of 30 million 80 kN equivalent single axle loads would also require an increase in high temperature binder grade.

SUMMARY

In one aspect, a method for automating mix design includes estimating volumetric properties for one or more mix designs; running one or more tests on the mix design using a gyratory compactor; digitally collecting data for each gyration from the gyratory compactor; and selecting an optimum mix based on the gyration data.

In a second aspect, a method for asphalt mix design includes predicting properties associated with a mix of volumetric properties; verifying properties of the mix by digitally collecting data for each gyration from a gyratory compactor; and selecting an optimum mix based on the gyration data.

In another aspect, a mix design system includes a gyratory compactor; and a computer coupled to the gyratory compactor, the computer having computer readable code to estimate volumetric properties for one or more mix designs; run one or more tests on the mix design using the gyratory compactor; digitally collect data for each gyration from the gyratory compactor; and select an optimum mix based on the gyration data.

Implementations of the above systems and methods may include one or more of the following. The above system can be used to design a Superpave mix. Five asphalt mixture types are specified in Superpave according to nominal maximum aggregate size: 9.5 mm, 12.5 mm, 19 mm, 25 mm, and 37.5 mm. Once binder and aggregate materials have been selected, various combinations of these materials are evaluated using a gyratory compactor. Three, and sometimes more, trial blends are evaluated. For example, assume that four aggregate stockpiles have been selected for use.

Once the trial blends have been established, a trial asphalt binder content is selected for each blend. The trial asphalt binder content is selected using an estimation procedure contained in Superpave or using a method for predicting volumetric properties disclosed in U.S. Pat. No. 5,943,234, the content of which is hereby incorporated by reference.

Next, two specimens of each trial blend are batched and compacted in the gyratory compactor and data is automatically collected, as detailed below. In addition, two specimens of each trial blend are produced and used to measure maximum theoretical specific gravity. The volumetric and densification characteristics of the trial blends are analyzed and compared with Superpave mix design criteria. The best trial blend that meets these criteria can be selected as the design aggregate structure.

The next step involves selection of the design binder content four different asphalt contents are tested(AC−05) (AC)(AC+0.5)(AC+1) after calculating volumetric properties, Optimum Binder is Calculated at 4% Air Void. The design aggregate structure containing the designed-selected blend at optimum asphalt binder content becomes the design asphalt mixture.

Advantages of the system may include one or more of the following. The system improves the efficiency of the user by minimizing the use of laboratory trial and error procedures.

DESCRIPTION

Figure 1:
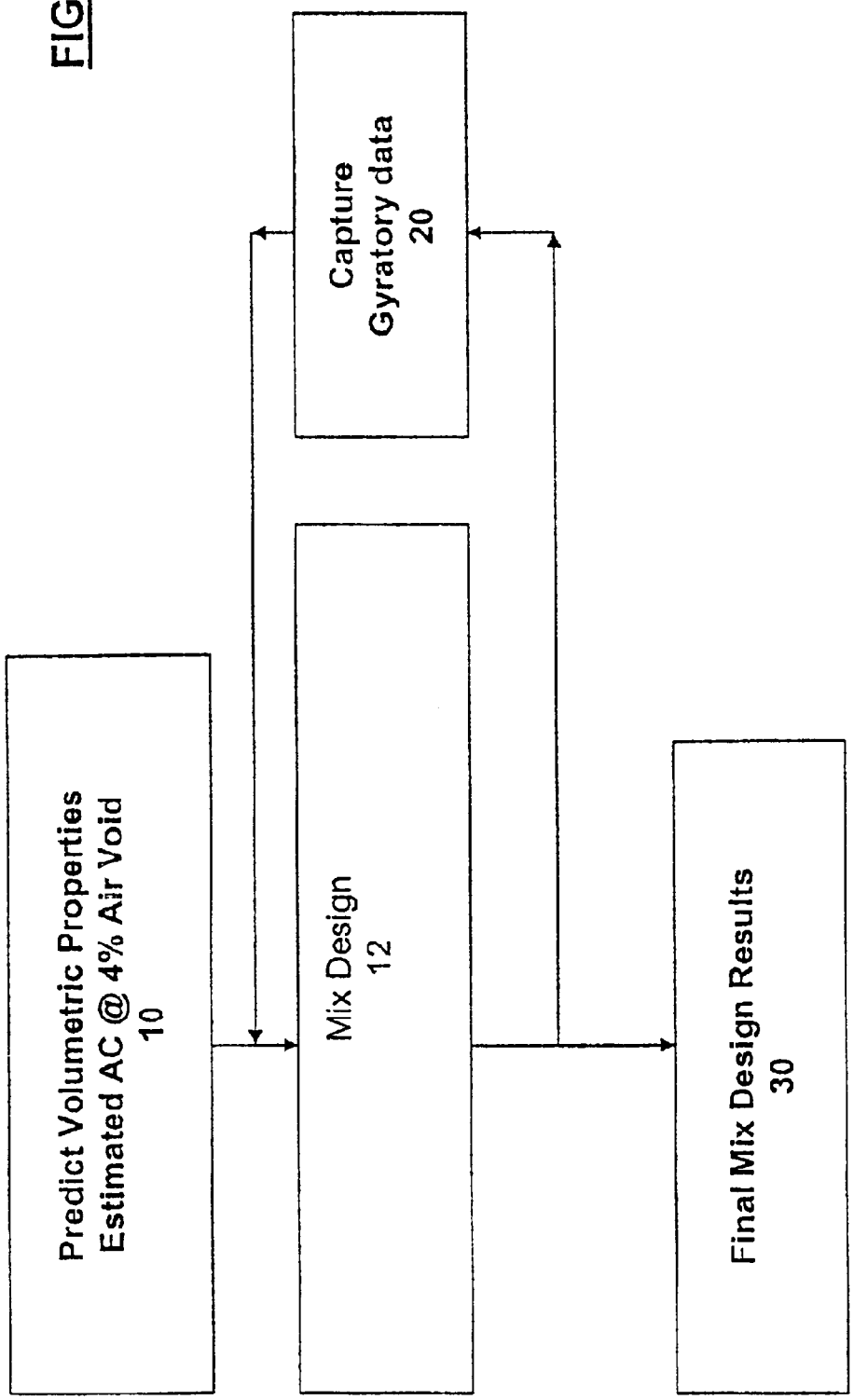
FIG. 1 shows a process for designing asphalt mixtures.

FIG. 1 shows a process for designing an asphalt mixture. First, volumetric properties are estimated (10). Next, a mix is designed (12). The mix can be the Superpave mix. During this process, gyratory data is automatically collected (20). The final mix is optimized (30).

Figure 2:
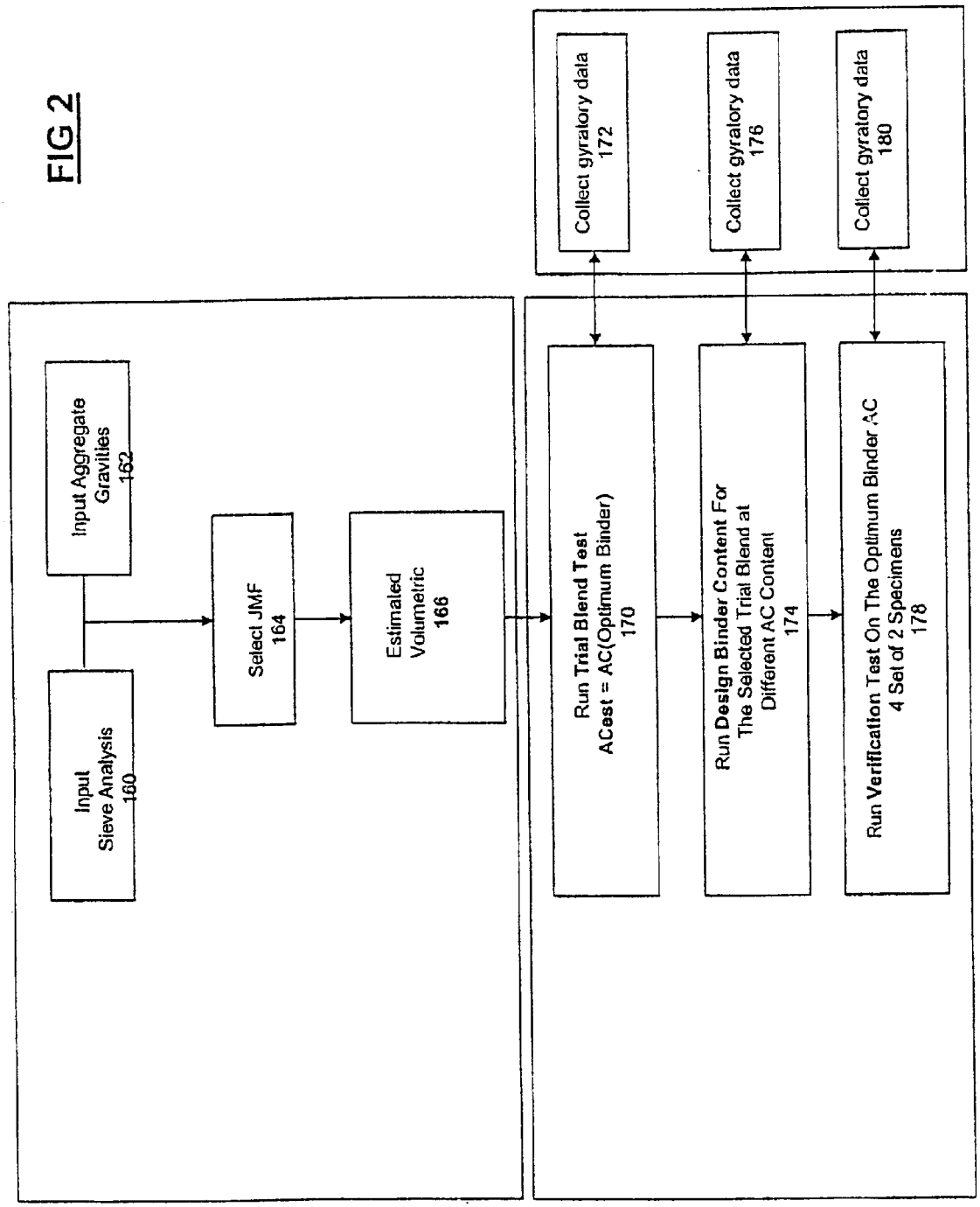
FIG. 2 shows one embodiment of the process of FIG. 1.

Referring now to FIG. 2, one embodiment for estimating mixture design is illustrated in more detail. The inputs to the process of FIG. 2 include performing sieve analysis (160) and inputting gravities data (162). The inputs received from blocks 160 and 162 are used to select a job mix formulation (JMF) (164). A variety of tools, including a graphical data entry tool, a computer optimized data entry tool, a forced data entry tool, and the manual data entry tool, are provided to select the JMF in block 164. Promising JMFs could be quickly evaluated using the estimation process provided by the present invention. JMFs which do not promote compliance of desired specifications can be quickly eliminated from expensive laboratory testing, saving the user time, labor and money. Thus, the present invention uses basic engineering properties to evaluate the proposed JMF and to test the proposed JMF for verification of the desired volumetric properties and to optimize the binder content. The present invention thereby allows the user to rapidly determine whether the proposed JMF, including the combination of aggregates and asphalts that defines the actual gradation and asphalt content to be obtained in the finished construction, satisfies the mixture design. The output of the JMF selection block 164 is provided to estimate volumetric properties with estimated AC Content @4% Air Void (166).

Next, the process of FIG. 2 performs laboratory verification of various proposed JMF solutions that may satisfy the requirements. First, a trial blend test is run based on estimated AC Content @4% Air Void (170). The test uses electronic data collection by a compactor control process of FIG. 1 (172). Based on the trial blend test, a trial blend is selected.

A design binder content test is run for the selected trial blend (174). The content test requests the process of FIG. 1 to generate gyratory data for the selected trial blend (176). Based on the design Binder Content test, an optimum binder is selected. From this selection, a verification test is run on the optimum binder (178). The verification test uses new gyratory data for the optimum binder Next, an illustrative Superpave Level I Mix Design procedure is discussed. By, asphalt and aggregate materials that meet their respective criteria are selected. The asphalt binders performance specification is based on the climate and attendant pavement temperatures in which the binder is expected to serve. Physical property requirements remain the same, but the temperature at which the binder must attain the properties change. The aggregate physical properties may be specified as coarse aggregate angularity, fine aggregate angularity, flat elongated particles, or by clay content, for example. Several trial blends are generated to meet Superpave gradation requirements (Coarse,Intermediate, Fine). Superpave uses the 0.45 power gradation chart with control limits and a restricted zone to develop a design aggregate structure. The aggregate Blend gradation may pass between the control points while avoiding the restricted zone. The maximum density gradation is drawn from 100% passing the maximum aggregate size through the origin.

Asphalt is blended with trial blends aggregate and run gyratory trial blend. Based on the volumetric test results, the best blend meeting the Superpave Level I Specification is selected.

Gyratory compaction test for the selected trial aggregate blend is performed with various design binder contents, and calculate the optimum binder at, for example, a 4% Air void from volumetric test results.

Another exemplary aggregate design process is detailed below:
1. Two specimens for each trial blend at estimated AC content (4% air void Target) are compacted using the superpave gyratory compactor. And specimens are also prepared for determination of the mixture maximum theoretical specific gravity Gmm (AASHTO T209).
2. Specimens are mixed at the appropriate temperature (165° C. to 172° C.) for the selected PG58-34 Binder. Specimens then short aged by placing the loose mix in a flat pan, in a forced draft oven at 135° C., for 4 hours. The specimens are then brought to compaction temperature range (151° C. to 157° C.). By placing them in another oven for short time less than 30 minutes.

The specimens are then removed and either
a) Compacted.
b) Allowed to cool loose for max theoretical specific gravity determination.

3. The number of gyrations used for compaction is determined based on the design high air temperature of the paving location and the traffic level, (ex. 38° C. 10–30 ESAL millions) The number of gyrations

4.

| @ Ninitial = | 8 gyrations |
| @ Ndesign = | 109 gyrations |
| @ Nmax = | 174 gyrations |

5. Each specimen will be compacted to the max number of gyrations with data is collected during the compaction process. (FIG. 1).
6. Knowing the initial mass of the mix. The fixed diameter of the mold, and the measured height, the density can be continually monitored.
7. After compaction, the final density of the specimen is determined by AASHTO T166.
8. The Gmm of each blend is also determined by AASHTO T209.
9. %Gmm (percent of maximum theoretical density) at each gyration can be determined, and corrected to match the final measured density of that specimen.

Volumetric Properties Determinations:

Volume: $V = 0.001 \times h \times 3.14 \times d^2/4$    V: volume of specimen
  h: height of specimen
  d: diameter of mold.
density: $Gmb_{(estimated)} = 100 \times W/V$    W: weight of specimen.
  Gsb: aggregates Bulk Specific gravity
Correction factor $C_{correct} = Gmb_{(measured)}/Gmb_{(estimated@Nmax)}$
Correct density: $Gmb_{(correct)} = C_{correct} \times Gmb_{(measured)}$
Precent of maximum theoretical density: $\% Gmm_{(correct)} = Gmb_{(correct)}/Gmm_{(measured)}$
Air Void: $Va = 100 - \% Gmm_{(correct)}$ @Ndesign
$VMA_{est} = 100 - \% Gmm_{(correct)}$ @Ndesign $\times Gmm_{(measured)} \times (100 - ACest)/(100 \times Gsb)$ 10. From the first (AC estimate) most on the time we cannot reach (4% Air Void). A second (AC estimate) is recalculated using correction factor. And Volumetric Properties are recalculated.

$\% AC_{(estimated\ @4\%\ Va)} = AC_{est} - 0.4 \times (4 - Va)$
$\% ACeff_{(estimated\ @4\%\ Va)} = \% AC_{(estimated\ @4\%\ Va)} - (100 - \% AC_{(estimated\ @4\%\ Va)}) \times Gs \times (Gse - Gsb)/(Gse \times Gsb)$
Dust Proportion: $DP = (\% P200)/(\% ACeff_{(estimated\ @4\%\ Va)})$
$VMA_{(est.@4\%\ Va)} = \% VMA_{est} + C \times (4 - Va)$
  $C = 0.1$ if $Va <= 4.0$
  $C = 0.2$ if $Va > 4.0$ -continued $$VFA_{(est\ @4\%Va)} = 100 \times (VMA_{(est.@4\%\ Va)} - 4)/VMA_{(est.@4\%\ Va)}$$
$$\% Gmm_{(est.@4\%\ Va)(correct@Nini)} = \% Gmm_{(trial)(correct@Nini)} - (4 - Va)$$
$$\% Gmm_{(est.@4\%\ Va)(correct@Nmax)} = \% Gmm_{(trial)(correct@Nmax)} - (4 - Va)$$

11. Check SUPERPAVE Level I Criteria for VMA, VFA, DP, % $Gmm_{@Nini}$, % $Gmm_{@Nmax}$ Select the best blend that pass the criteria, and run design binder content at:

[AC−0.5], [AC], [AC+1], [AC+0.5]

12. Two specimens for each AC content are compacted using the superpave gyratory compactor and the process of FIG. 2. And specimens are also prepared for determination of the mixture maximum theoretical specific gravity Gmm (AASHTO T209).

13. Volumetric Properties are calculated @ each AC content, and Optimum Binder is calculated @ 4% airVoid. The volumetric properties are checked against the Criteria for SUPERPAVE Level I.

14. Densification Curves are plotted for every specimen from the collected data using the process of FIG. 2.

(X=Number of Gyration, Y=%Gmm)

Figure 3:
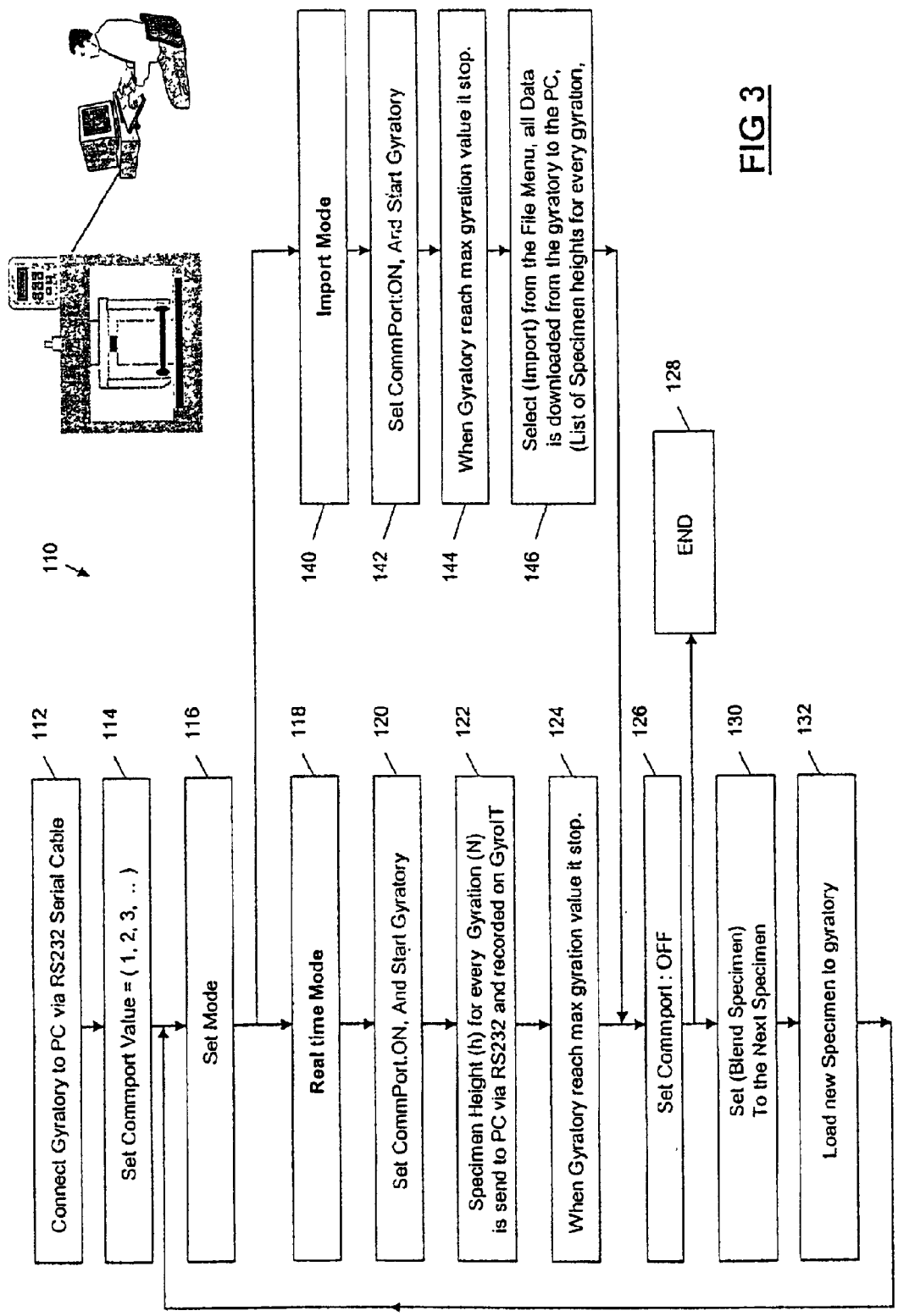
FIG. 3 shows a process for performing gyratory compaction and collecting gyratory data to be used in the process of FIG. 2.

FIG. 3 shows a process 110 for performing gyratory compaction and collecting gyratory data to be used in the process of FIG. 2. First, the user selects a gyratory equipment type (112). The equipment can be a unit commercially available from a variety of vendors, Pine Instrument Company of Grove City, Pa.; and Troxler Electronic Laboratories, Inc. of Research Triangle Park, N.C. Next, the user sets up communications port with the selected equipment (114). The user selects a display mode: Real Time or Import from a file (116). If the user selects Real Time mode (118), the process 110 turns on the communication port and starts the gyratory compactor/equipment (120). Next, the gyratory compactor measures a specimen height for each gyration and the resulting information is captured (122). When the gyratory compactor reaches a predetermined maximum gyration value, the gyratory compactor is turned off (124). Next, the communication port is turned off (126).

The process 110 then determines whether another specimen needs to be tested. If not, the process 110 exits (128). Alternatively, the next specimen is selected (130) and the new specimen is loaded into the gyratory compactor (132). The process then loops back to allow the user to set the mode (116). From the mode selection (116), the user can select an import mode (140). In this mode, the communication port is turned on and the gyratory compactor is started (142). The process monitors the gyratory compactor and when the maximum gyration value is reached, the process stops (144). Data stored in the gyratory compactor is captured (146) and downloaded for volumetric properties calculation. Next, the process 110 jumps to 124 and turns off the gyratory compactor.

The above processes can be implemented as software running on a computer. The preferred software embodiment worlds with Microsoft's Windows operating system, including Windows-98, Windows-NT and Windows-XP, although any other suitable graphical operating system such as MacOS and Solaris can be used. Windows is a graphical-based operating environment, also known as a graphical user interface, or (GUI) that allows multitasking of programs. In Windows, the computer screen operates like a desktop, allowing instantaneous access to clocks, spreadsheets, word processing, communication software, graphics packages and, of course, this mix design program. The user is able to select rapidly among those applications, as well as any others developed for the environment. The ability to work simultaneously on several different projects more closely approximates the manner in which most people work. However, the user can work in one program at a time if desired. Preferably, the software of the invention is an object-oriented software constructed from Visual Basic, although it can be written in a number of other languages.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for automating mix design, comprising:
   estimating volumetric properties for one or more mix designs;
   running one or more tests on the mix design using a gyratory compactor;
   digitally collecting data for each gyration from the gyratory compactor; and
   selecting an optimum mix based on the gyration data.

2. The method of claim 1, further comprising turning on a communication port.

3. The method of claim 1, further comprising selecting an operating mode.

4. The method of claim 1, further comprising capturing a specimen height for each gyration from the gyratory compactor.

5. The method of claim 1, further comprising turning off the gyratory compactor upon reaching a predetermined gyration value.

6. The method of claim 1, further comprising turning off the communication port.

7. The method of claim 1, further comprising loading a second specimen.

8. The method of claim 1, further comprising uploading data to a computer.

9. A method for asphalt mix design, comprising:
   predicting properties associated with a mix of volumetric properties;
   verifying properties of the mix by digitally collecting data for each gyration from a gyratory compactor; and
   selecting an optimum mix based on the gyration data.

10. The method of claim 9, further comprising:
    turning on a communication port;
    selecting an operating mode;
    capturing a specimen height for each gyration from the gyratory compactor; and
    turning off the gyratory compactor upon reaching a predetermined gyration value.

11. A system, comprising:
    a gyratory compactor; and
    a computer coupled to the gyratory compactor, the computer having computer readable code to estimate volumetric properties for one or more mix designs; run one or more tests on the mix design using the gyratory compactor; digitally collect data for each gyration from the gyratory compactor; and select an optimum mix based on the gyration data.

12. The system of claim 11, further comprising code to turn on a communication port.

13. The system of claim 11, further comprising code to select a real-time mode or an import mode.

14. The system of claim 11, further comprising capturing a specimen height for each gyration from the gyratory compactor.

15. The method of claim 11, further comprising code to turn off the gyratory compactor upon reaching a predetermined gyration value.

16. The system of claim 11, further comprising code to turn off the communication port.

17. The system of claim 11, wherein the gyratory compactor sequentially receives one or more specimen.

18. The system of claim 11, further comprising code to upload gyratory data to a computer.

19. The system of claim 11, wherein the code to receive one or more material properties further comprises code to turn on the gyratory compactor.

20. The system of claim 11, wherein the mix comprises a Superpave mix.

* * * * *